United States Patent
Antar et al.

[11] Patent Number: 5,827,210
[45] Date of Patent: Oct. 27, 1998

[54] ORTHOPEDIC CAST WALKER BOOT

[75] Inventors: Morris Antar, New York, N.Y.; Victor M. Nunes, Cumberland, R.I.

[73] Assignees: Comed Inc., New York, N.Y.; Johnson & Johnson Professional, Inc., New Brunswick, N.J.

[21] Appl. No.: 625,165

[22] Filed: Apr. 1, 1996

[51] Int. Cl.[6] ..................................................... A61F 5/01
[52] U.S. Cl. ............................... 602/23; 36/110; 602/10; 602/27
[58] Field of Search .............................. 36/110, 131, 140, 36/1.5, 88; 602/12, 16, 23, 27, 10, 26

[56] References Cited

U.S. PATENT DOCUMENTS

| | | |
|---|---|---|
| 3,955,565 | 5/1976 | Johnson, Jr. ................................ 602/12 |
| 4,280,489 | 7/1981 | Johnson, Jr. . |
| 4,563,825 | 1/1986 | Tesser ........................................ 36/131 |
| 4,771,768 | 9/1988 | Crispin ....................................... 602/16 |
| 5,078,128 | 1/1992 | Grim et al. . |
| 5,370,133 | 12/1994 | Darby et al. . |

*Primary Examiner*—Paul T. Sewell
*Assistant Examiner*—Anthony Stashick
*Attorney, Agent, or Firm*—Ezra Sutton

[57] ABSTRACT

An orthopedic cast walker boot, that includes a tubular enclosure formed of a semi-flexible material having a first section member for covering the rear of the calf, ankle, heel, and sole of the foot; and a second section member for interfitting with the first section member; the second section member having an upper section for covering the shin area of the leg, and a lower section for covering the top area of the foot. The upper and lower sections being integrally connected by a pliable and flexible intermediate connecting section having multiple joints. Velcro fastening straps are provided for fastening and enclosing the first and second section members to form the tubular enclosure about the leg, the ankle, and the foot of the wearer; and traction treads means are adhesively attached to the bottom surface of the first section member.

13 Claims, 6 Drawing Sheets

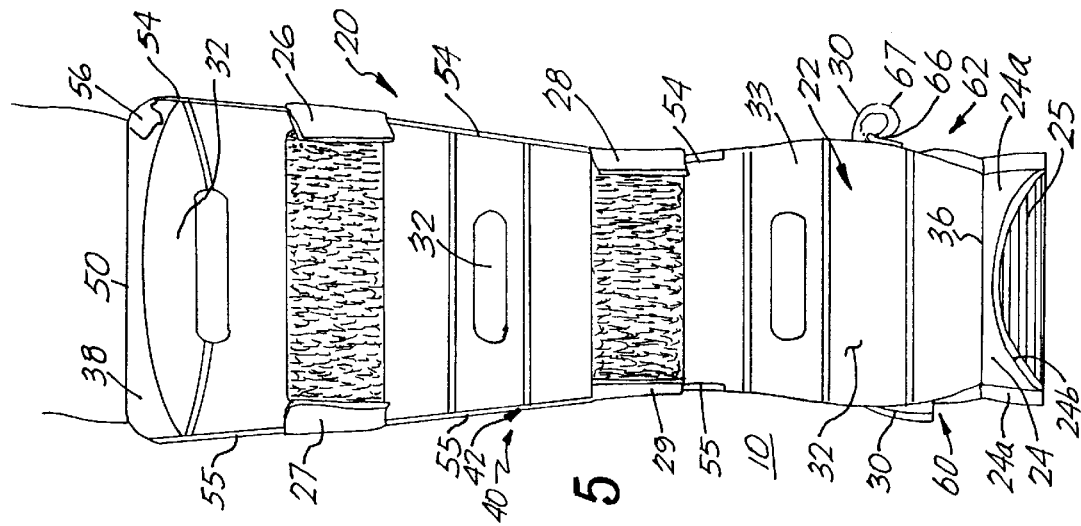
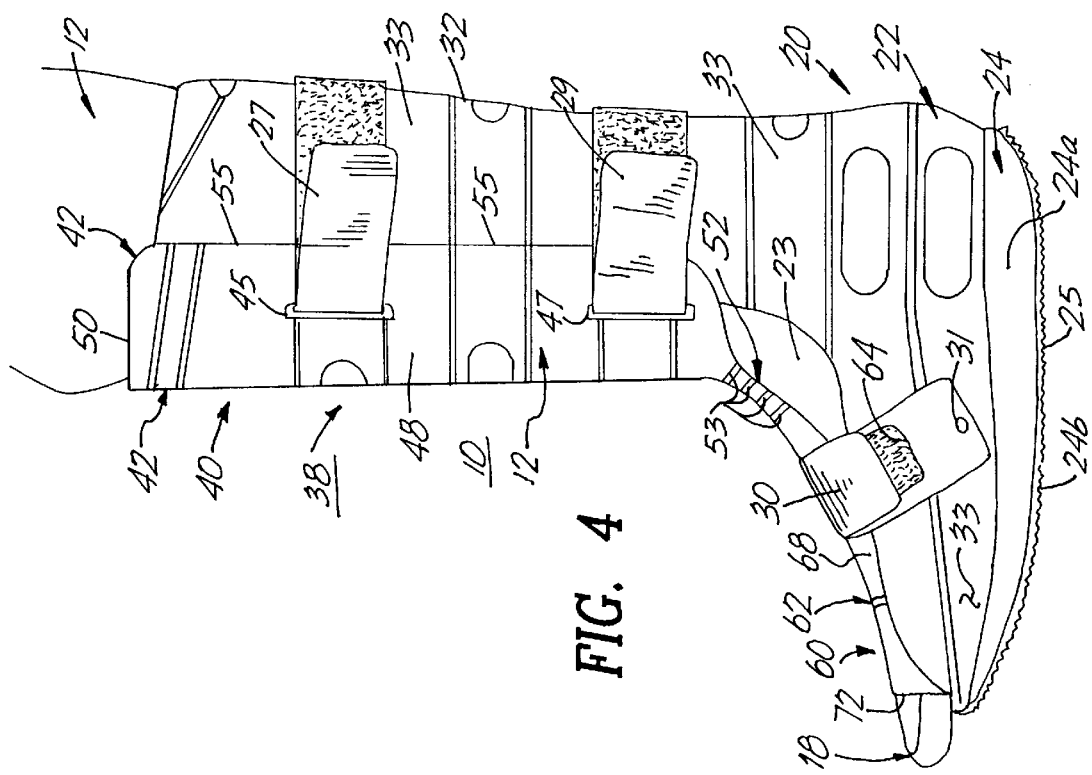

ORTHOPEDIC CAST WALKER BOOT

FIELD OF THE INVENTION

The present invention relates to a new and improved orthopedic cast walker boot for immobilizing the foot, ankle and lower leg, including the calf and shin portions which are below the knee. The cast walker boot acts as a substitute for a rigid plaster or fiberglass cast. More particularly, the improved cast walker boot provides uniform compression over the lower leg, ankle and foot areas and allows the compression to be focused and conformable to any given section of the boot for the wearers' comfort.

1. Background of the Invention

Conventional casts for the lower leg, ankle, and/or foot have been made of plaster of paris or fiberglass. More recently, casts have been made from semi-rigid or rigid plastic shells having interior areas that have padding or cushion means for protecting the injured areas while giving the correct orthopedic support for proper healing of the injured leg, ankle or foot. Typically, these casts are made of a single-piece or two-piece construction having means to apply compression to the injured or surgically operated area of the lower leg, ankle or foot.

It would be highly desirable to have a cast walker boot which is adjustable so as to provide a uniform compression to the injured area of the lower leg, ankle and/or foot, and where increased adjustability is obtained by having a two-sectioned boot design of a special type for proper shin compression.

2. Description of the Prior Art

Orthopedic cast walker boots of various designs, styles, and materials of construction have been disclosed in the prior art. However, the prior patents in this field have a number of drawbacks. For example, U.S. Pat. No. 3,955,565 discloses an orthopedic cast apparatus formed of two complementary shaped half-shell members fabricated from a thin and rigid plastic material. The rear shell member fits about the calf, ankle, heel and sole of the foot; and the front shell member fits about the shin of the lower leg and the top area of the foot. However, this construction does not provide sufficient support and comfort to the injured areas, as this cast has limited capability to apply uniform compression to the affected and injured areas.

U.S. Pat. Nos. 5,370,133,; 5,078,128; 4,771,768; and 4,280,489 all disclose immobilization braces in the form of a single-part, short length walker made of a semi-flexible molded plastic material for applying controlled and uniform compression to the injured, traumatized, or surgically-operated areas of the lower leg, ankle or foot. These patents show the boot walker to be of a single-piece construction, whereas the present invention is of a two-piece construction.

Accordingly, it is an object of the present invention to provide an orthopedic cast walker boot for easily and quickly immobilizing the lower leg, ankle and/or foot of the wearer's injured or surgically-operated areas.

Another object of the present invention is to provide a cast walker boot made of plastic foam having a rubber sole which is light in weight and comfortable to wear.

Another object of the present invention is to provide a cast walker boot that is made of a two-section construction having a first section covering the calf, heel and sole areas, and a second section covering the shin area, and the top area of the foot, such that the compression can be focused and made conformable to any given section of the boot for the wearers' comfort by adjusting the securing Velcro straps.

Another object of the present invention is to provide a cast walker boot that has easily adjustable compression means for giving a controlled and uniform pressure to the injured, traumatized, or surgically operated area(s) of the lower legs, ankle or foot.

A further object of the present invention is to provide a cast walker boot having simple instructions for wearing and adjusting the boot for a medically proper fit for the wearers' needs.

A still further object of the present invention is to provide a cast walker boot that can be mass produced in an automated and economical manner.

SUMMARY OF THE INVENTION

In accordance with the present invention, there is provided an improved orthopedic cast walker boot forming a tubular enclosure for enclosing the calf and shin portions of the leg, the ankle, and a portion of the foot. This cast walker boot is used when an injury to the lower leg extremity occurs, such as a broken bone, an ankle ligament tear or an Achilles tendon tear. After being attended by a physician or other medical personnel, the cast walker boot is used to immobilize the lower leg extremity and give the wearer the proper support, mobility and adjustment capability for walking while letting the injured leg heal without causing any pain or discomfort to the wearer. The cast walker boot may be made in various sizes, colors, patterns and designs that will fit adults and children.

The tubular enclosures comprises first and second section members which in an assembled state form the orthopedic cast walker boot of the present invention that is fitted about the traumatized lower leg extremity. There are a plurality of fastening structures in the form of Velcro closure straps for attaching the second member to the first section member which forms the tubular enclosure in the assembled configuration. The cast walker boot has a permanently attached rubber sole with a traction tread for ease and comfort of waling with the cast.

The cast walker boot is made of a semi-flexible, molded material such as a high density styrofoam, plastic or fiberglass. Each section member is machine molded to shape. When in use, in the assembled state, the wearer or medical personnel can readjust the fastening straps to provide the proper compression and comfort to the wearer, such that, proper healing can occur, without causing any pain, discomfort or further injury to the user.

BRIEF DESCRIPTION OF THE DRAWINGS

Further objects, features, and advantages of the present invention will become apparent upon consideration of the detailed description of the presently-preferred embodiments, when taken in conjunction with the accompanying drawings, wherein:

FIG. 4 is a side view of the cast walker boot showing the fastening and compression means in an assembled state fitted about the lower leg extremity;

FIG. 5 is a rear view of the cast walker boot showing the rear section member and boot heel in an assembled state;

DETAILED DESCRIPTION OF THE PREFERRED EMBODIMENT

Figure 1:
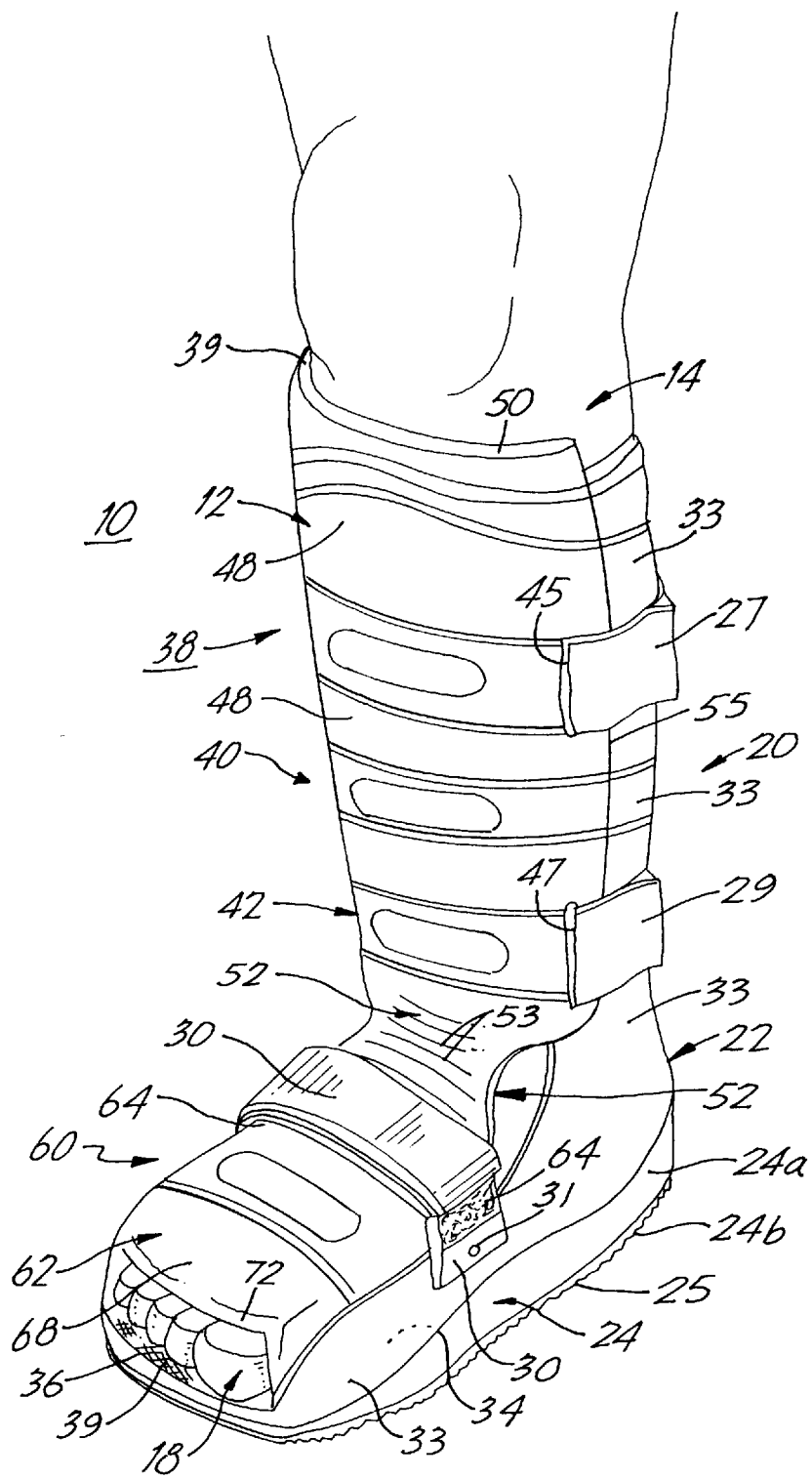
FIG. 1 is a front perspective view of the present invention showing the orthopedic cast walker boot in an assembled state, fitted about the lower leg extremity.
Figure 2:
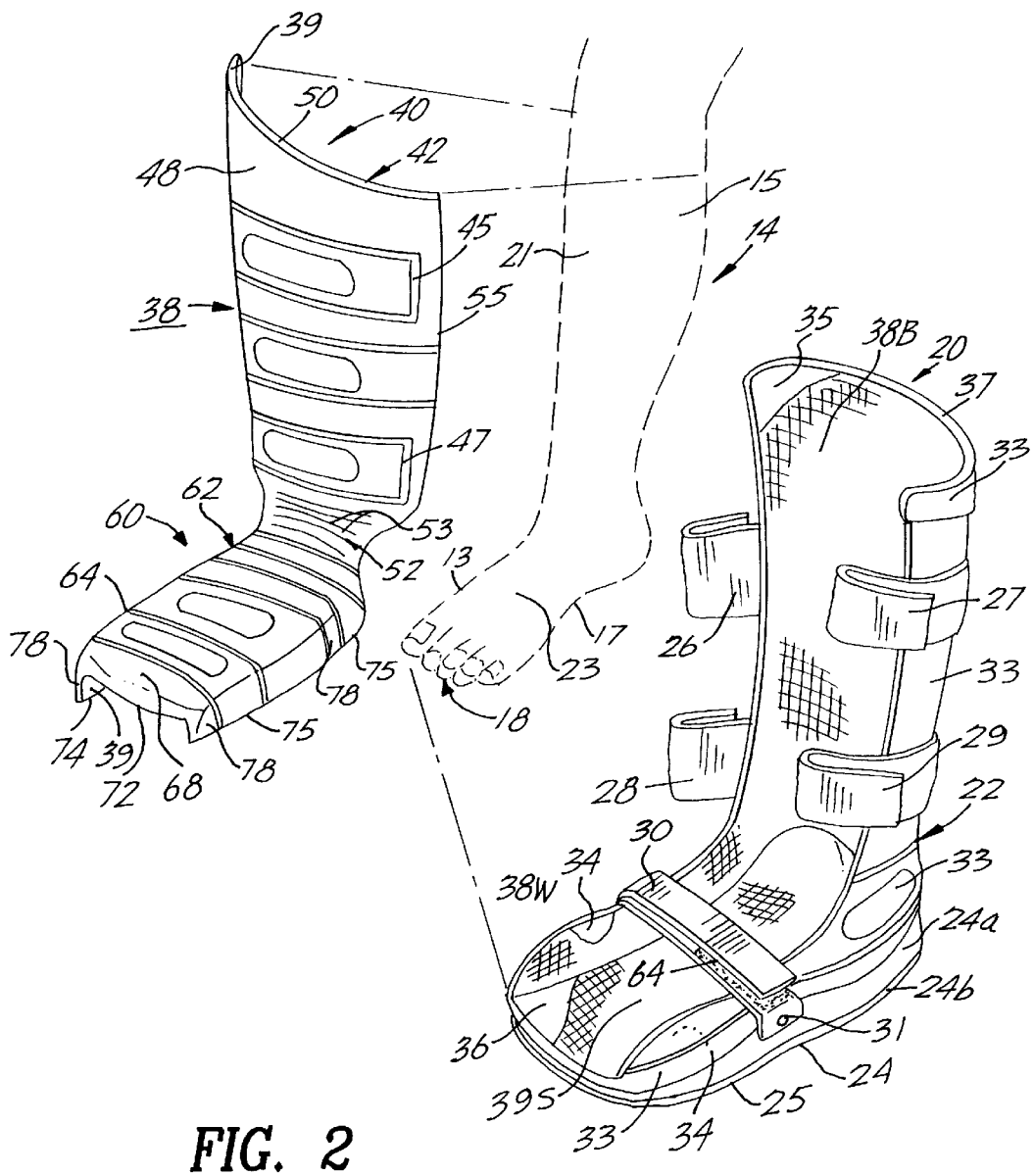
FIG. 2 is an exploded perspective view of the orthopedic cast walker boot showing the two sections of construction and also depicting the fastening and compression means for the boot.

The orthopedic cast walker boot 10 and its component parts are represented in FIGS. 1 through 9. FIG. 1 shows the cast walker boot 10 having a tubular enclosure 12, including a first section member 20, and a second section member 38 in an assembled state fitted about the lower leg extremity 14 of a user. FIG. 2 shows the component parts and the sequential placement of the sections of the boot 10.

First section member 20 having a rear styrofoam structure 22 is fixedly attached to a rubber sole 24 and is used for receiving the calf 15, ankle 16, sole 17 and heel 19 of the foot 13 of an injured person. The second section member 38 having a front shin styrofoam structure 42 is used for receiving and covering the shin area 21 of the lower leg 14. The second section member 38 also includes a foot top styrofoam structure 62 which is used for receiving and covering the top 23 of the foot 13 area of the injured user.

Figure 8:
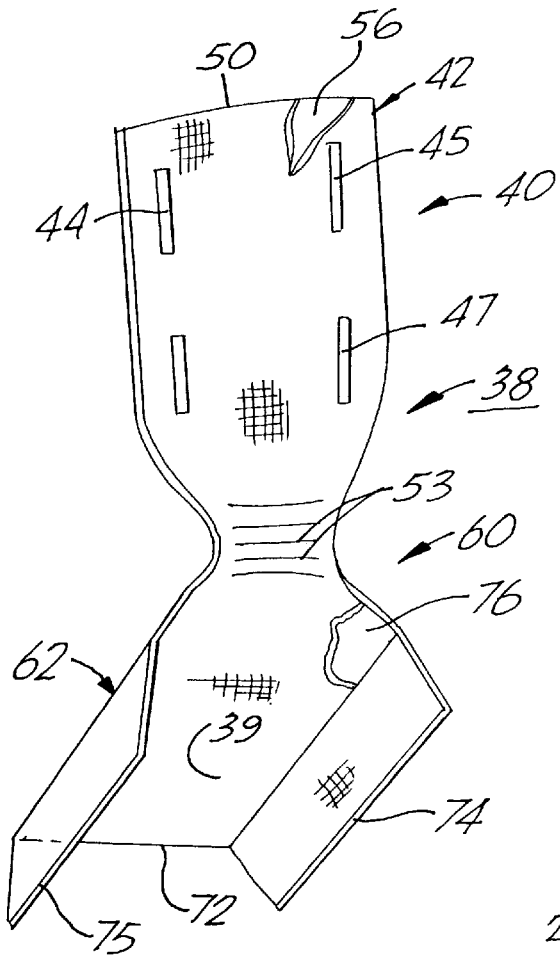
FIG. 8 is a top rear perspective view of the shin section and top of foot section showing the inside surface area of those sections.

FIGS. 3, 4, 5, 6 and 7 show the orthopedic cast walker boot 10, in detail with different views depicting the plurality of fastening straps 26, 27, 28, 29, and 30 on a lower leg extremity 14 of a user in a fastened state and showing the proper closure of the cast walker boot 10. FIG. 8 shows the shin structure 42 and front foot structure 62, from a rear perspective, depicting the fabric material padding 39 being attached to the inside surface areas 56 and 76.

FIG. 1 shows the orthopedic cast walker boot 10 in an assembled state comprising a tubular enclosure 12 made of a firm, flexible molded material like, ie. high density styrofoam, plastic or fiberglass, for enclosing a calf portion, the ankle, and a portion of one foot and leg. The cast walker boot 10 is produced in various sizes, colors and designs to fit adults and children. As shown in FIGS. 1 and 2, the tubular enclosure 12 has a first section 20 having a rear structure 22 which covers and seats calf 15, ankle 16 sole 17 and heel 19 of the foot 13 to bring them in contact with inner fabric material 38W, 38B, and 39S. The rear structure 22 is an L-shaped, contiguous molded section having an outer backwall 32, outer side walls 33, inner side walls 34, an inner backwall 35 and an inner bottom wall 36. Cotton padded fabric material 38W, 38B, and 39S is permanently affixed to the inner side walls 34, back wall 35 and bottom wall 36, respectively, by means of gluing and/or stitching, such that the padded fabric material 38W, 38B and 39S cushions the calf 15, ankle 15, heel 19 and sole 17 of the wearer's foot 13, when the leg and foot fastening straps 27, 29, and 30 are tightened around the lower leg extremity 14 of the wearer. A rubber sole 24 is permanently attached by gluing to the bottom wall 36 of rear structure 22. The rubber sole includes an upper thick rubber sole 24a and a thin lower rubber sole 24b having a plurality of ridges 25 for proper traction, as depicted in FIG. 10.

Figure 3:
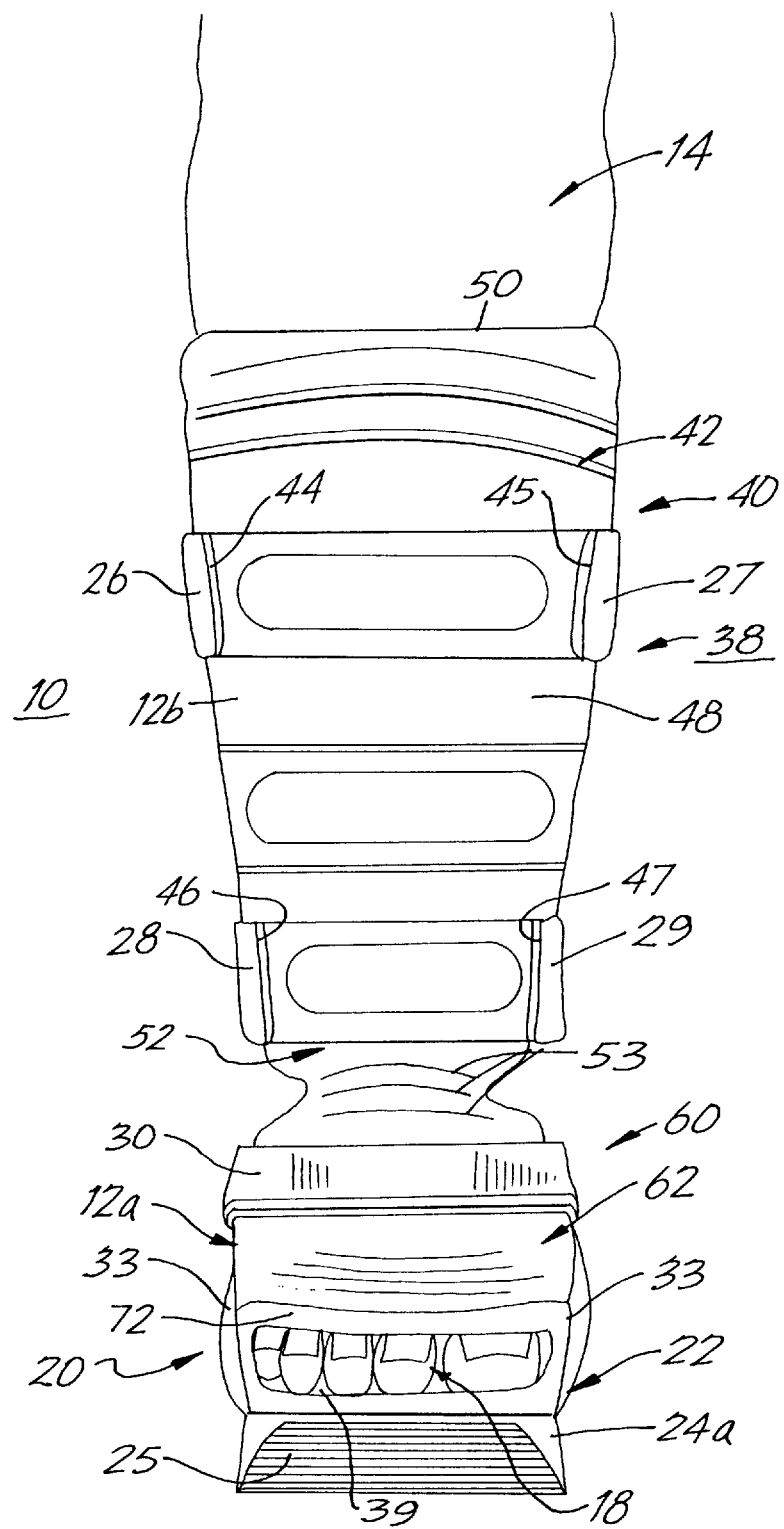
FIG. 3 is a front view of the cast walker boot showing the shin and front foot sections in an assembled state fitted about the lower leg extremity.
Figure 6:
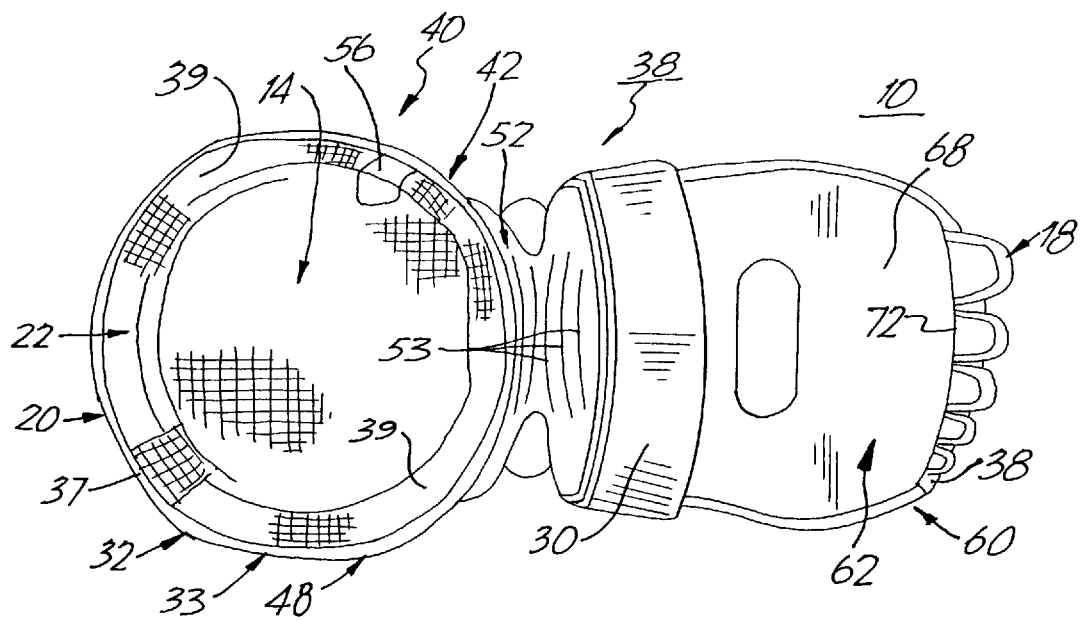
FIG. 6 is a top view of the cast walker boot showing the shin and front foot sections in an assembled state.
Figure 7:
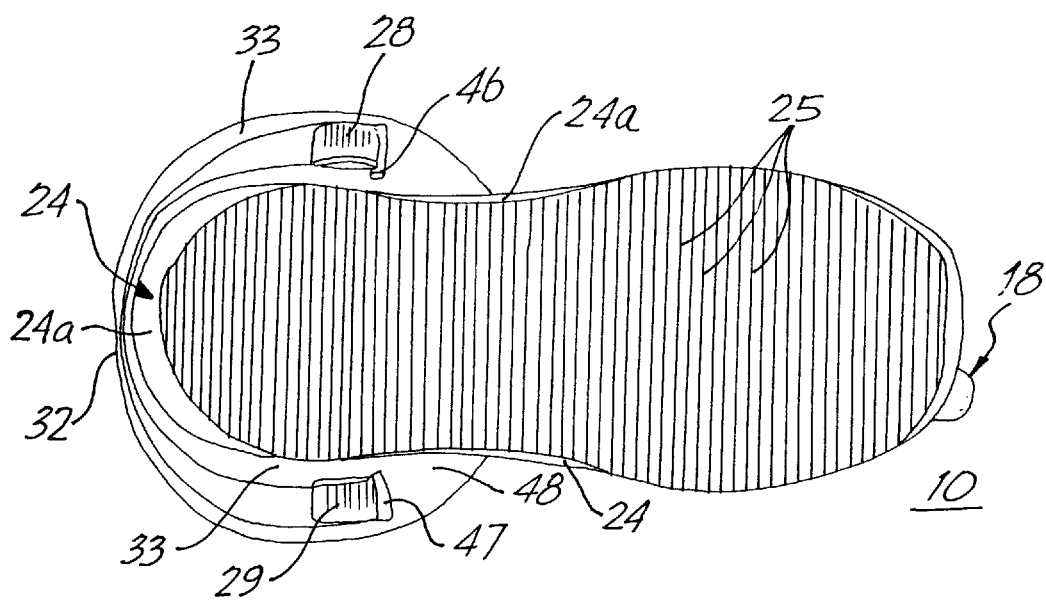
FIG. 7 is a bottom view of the cast walker boot showing the rubber sole of the boot.
Figure 9:
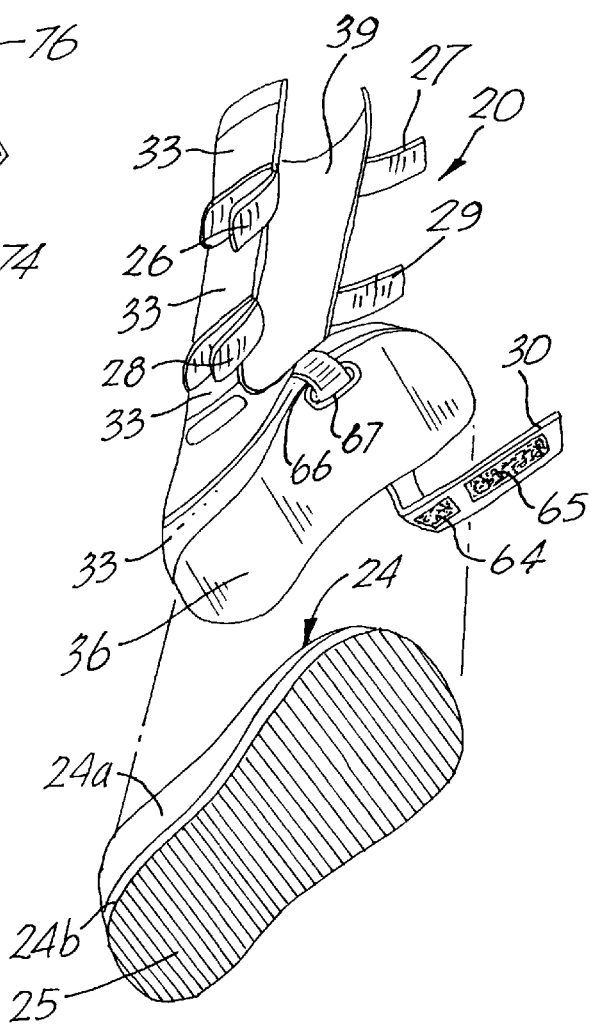
FIG. 9 is an exploded bottom front perspective view of the rear foot and leg sections showing the rubber sole attached to the bottom rear section to form the first section member.

The rear structure 22 of the first section 20, also includes upper and lower shin fastening straps 26, 27, 28, 29, and bottom foot strap 30 permanently attached by riveting, gluing, or stitching to the outer side walls 33. Fastening straps 26, 27, 28, 29, and 30 include Velcro material which gives the user a varied control of the amount of tightness or compression given to an injured area. First section member 20 further includes a strap loop 66 having a strap ring 67. Strap loop 66 is fixedly connected to the outside wall 33 by means of gluing, riveting, or stitching, as shown in FIG. 9. Strap 30 is passed through ring 67 and closed upon itself with Velcro tabs 64, 65 which secures the lower section 60 to the first section member 20 of boot 10. The fastening strap 30 is attached to the outside surface area 33 by a rivet pin 31, as shown in FIG. 1. The securing of the first section member 20 with the lower section 60 with strap 30 forms a lower foot tubular enclosure 12a of second section member 38 when attached, as depicted in FIG. 3.

As shown in FIGS. 1, 2, and 8, the second section member 38 has upper section member 40, an intermediate connecting section 52, and a lower section member 60. The upper section member 40 of tubular enclosure 12 has a front shin, convex structure 42 which is positioned and fastened to the shin area 21 of the lower leg 14 by the use of the upper and lower shin fastening straps 26, 27, 28 and 29 of the first section 20. The shin structure 42 has upper and lower strap openings 44, 45, 46 and 47 for receiving fastening straps 26, 27, 28 and 29, as shown in FIGS. 2 and 8. Shin structure 42 further includes and outside surface 48, an inside surface 56 and an upper edge 50. A cotton padded fabric 39 is permanently attached to the inside surface 56 by means of gluing and/or stitching, such that the padded fabric 39 cushions the shin area 21, when the fastening straps 26, 27, 28 and 29 are tightened around the lower leg 14. When the front shin structure 42 of upper section 40 is in its assembled state with the rear structure 22 of first section 20 by means of the enclosure straps 26, 27, 28 and 29, this forms the upper leg tubular enclosure 12b, as depicted in FIG. 3.

As shown in FIGS. 1, 2 and 9, the lower section member 60 of tubular enclose 12 has a convex, foot top structure 62 which is positioned and fastened to the top area 23 of the foot 13 by the use of bottom foot fastening strap 30 attached to the sidewall 33 of structure 22 of first section 20. Foot top structure 62 includes an outside surface 68, and inside surface 76, and a front edge 72. The strap 30 is looped through adjustment ring 67 and closed by use of Velcro tabs 64 and 65. A cotton padded fabric 39 is also permanently affixed to the inside surface 76 by means of gluing and/or stitching, such that the padded fabric 39 cushions the top area 23 of foot 13, when the foot fastening strap 30 is tightened around the foot 13.

Intermediate connecting section 52 includes a plurality of pliable and flexible joints 53 for conforming the second section member 38 on the users lower leg 14 and foot 13. Intermediate connecting section 52 integrally connects the upper and lower sections 40 and 60 with each other.

OPERATION OF THE PRESENT INVENTION

A person having a broken leg or torn ligament in the ankle, or an Achilles heel trauma, being surgically repaired by a physician, would use the orthopedic cast walker boot 10. The cast walker boot 10 immobilizes the lower leg 14 extremity and gives the user proper support, mobility and an adjustment capability for walking while letting the injured area heal and recuperate over time for proper mending without causing pain or discomfort to the user.

After being attended by medical personnel for the leg, ankle or foot trauma, the medical personnel initially places the rear structure 22 of the first section 20 of cast walker boot 10 along the calf 15, ankle 16, heel 19, and sole 17 of the foot 13.

Once fitted with first section 20, the attending medical personnel then places the second section member 38 such that the convex foot-top structure 62 of the lower section 60 is placed on the top area 23 of the foot 13, and simultaneously, the convex shin structure 42 of the upper section 40 is placed on the shin area 21 of the lower leg 14, as depicted by FIG. 1. Proper alignment of the foot structure 62 on the foot 13 occurs when bottom edges 74 and 75 of foot structure 62 meet the inside bottom wall 36 of the rear structure 22 of first section 20, and when outside walls 78 abut and meet the inside walls 34. The medical personnel then secures the foot 13 by fastening the foot enclosure strap 30 of rear structure 22 through loop ring 67 and closed by the Velcro receiving pads 64 and 65. This insures the proper enclosure of foot 13 within the tubular enclosure 12a of cast walker boot 10. Only the toes 18 of the user are exposed along edge 72 of the foot structure 62.

Similarly, proper alignment of the shin structure 42 on the shin area 21 occurs when side edges 54 and 55 of shin structure 42 overlap the front edge 72 of foot structure 62 and the outside walls 33 of rear structure 22, as depicted in FIGS. 1, 3 and 4 of the drawings. The medical personnel then slips the upper and lower fastening straps 26, 27, 28 and 29 of rear structure 22 through their corresponding strap slot upper and lower openings 44, 45, 46 and 47 and then tightens the straps 26, 27, 28, and 29 around the shin area 21 of the lower leg 14 for the proper comfort and compression of the traumatized leg 14 of the user. This insures the proper enclosure of leg 14 within the tubular enclosure 12b of cast walker boot 10. Only the knee area and above are exposed along edges 50 and 37 of tubular enclosure 12 of cast walker boot 10, as shown in FIG. 1. This completes the initial enclosure and immobilization of the traumatized area of the lower leg extremity of a person using the orthopedic cast walker boot.

Intermediate connecting section 52 is pliable and flexible via flexible joints 53 and allows maximum conformability of the upper section 40 to the shin area 21 and of lower section 60 to the top area of foot 23, so that when straps 26, 27, 28, 29, and 30 are tightened section 52 easily flexes and conforms to the swollen areas of the foot 13 and shin 21. Thereafter, the cast walker boot 10 is easily adjusted by straps 26, 27, 28, 29, and 30 as the swelling decreases.

As the leg 14 mends, and swelling of the injured area decreases, the user and/or medical staff may re-adjust all fastening straps 26, 27, 28, 29, and 30 to a new comfort and compression level. Also, the cast walker boot may have loosened somewhat on the leg 14 of the user, and re-adjustment may be necessary for this reason.

Once the injured leg has mended properly, the medical staff and/or user reverses the aforementioned process by removing the shin structure section 42 first; the foot structure section 62 second; and the rear structure 22 last.

ADVANTAGES OF THE PRESENT INVENTION

Accordingly, an advantage of the present invention is that it provides an orthopedic cast walker boot for easily and quickly immobilizing the lower leg, ankle and/or foot of the wearer's injured or surgically operated areas.

Another advantage of the present invention is that it provides for a cast walker boot made of plastic foam having a rubber sole which is light in weight and comfortable to wear.

Another advantage of the present invention is that it provides a cast walker boot that is made of a two-section construction having a first section covering the calf, heel and sole areas, and second section covering the shin area, and the top area of the foot, such that the compression can be focused and conformable to any given section of the boot for the wearers' comfort by adjusting the securing Velcro straps.

Another advantage of the present invention is that it provides a cast walker boot that has easily adjustable compression means for giving a controlled and uniform pressure to the injured, traumatized or surgically operated areas of the lower legs, ankle or foot.

A further advantage of the present invention is that it provides for a cast walker boot having simple instructions for wearing and adjusting the boot for a medically proper fit for the wearers' needs.

A still further advantage of the present invention is that it provides for a cast walker boot that can be mass produced in an automated and economical manner.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. An orthopedic cast walker boot, comprising:

a) tubular enclosure formed of a semi-flexible material having a first section member for covering the rear of the calf, ankle, heel and sole of the foot;

b) a second section member for interfitting with said first section member; said second section member having an upper front section for covering the shin area of the leg, and a lower front section for covering the top area of the foot;

c) said upper and lower front sections being integrally connected by a pliable and flexible intermediate front connecting section having multiple joints; said multiple joints providing a non-rigid, flexible connection for conforming said front sections to the user's shin, foot and ankle areas;

d) said intermediate front connecting section being narrower than and more pliable and flexible than said upper and lower front sections;

e) fastening means for fastening and enclosing said first and second section members to form said tubular enclosure about the leg, the ankle and the foot of the wearer; and f) traction means adhesively attached to the bottom surface of said first section member.

2. An orthopedic cast walker boot in accordance with claim 1, wherein said semi-flexible tubular enclosure is formed of high density styrofoam, plastic or fiberglass.

3. An orthopedic cast walker boot in accordance with claim 1, wherein said first and second section members are molded into a shape to conform to the leg and foot.

4. An orthopedic cast walker boot in accordance with claim 1, wherein said fastening means are hook and loop fasteners.

5. An orthopedic cast walker boot in accordance with claim 1, wherein said traction means are in the form of a rubber, neoprene or plastic sole covering.

6. An orthopedic cast walker boot in accordance with claim 5, wherein said sole covering has an upper sole section, and a lower sole section having one side with molded geometric shaped treads for proper traction when walking.

7. An orthopedic cast walker boot in accordance with claim 1, wherein said first section member includes contiguous sidewalls integrally connected to a back wall and bottom wall to form a convex contour structure which conforms to the shape of the calf; ankle; sole and heel portions of the foot.

8. An orthopedic cast walker boot in accordance with claim 1, wherein said second section member has a convex contour to conform to the shape of the shin area of the lower leg.

9. An orthopedic cast walker boot in accordance with claim 1, wherein said second section member includes contiguous sidewalls integrally connected to a top wall to form a convex contour structure which conforms to the shape of the top of the foot.

10. An orthopedic cast walker boot in accordance with claim 1, wherein said fastening means of said first section member are fixedly attached to the outside surface thereof by means of gluing or stitching.

11. An orthopedic cast walker boot in accordance with claim 1, wherein said first and second section members have a cotton padded fabric fixedly attached to the inside surfaces of each section by means of gluing or stitching for the comfort of the wearer.

12. An orthopedic cast walker boot in accordance with claim 1, wherein said tubular enclosure includes a front opening for the toe portion of the foot and an upper opening for the calf and shin portion of the leg.

13. An orthopedic cast walker boot in accordance with claim 1, wherein said tubular enclosure is molded in various sizes, colors, and design shapes to fit adults and children.

* * * * *